(12) United States Patent
Takeuchi et al.

(10) Patent No.: US 7,271,288 B2
(45) Date of Patent: Sep. 18, 2007

(54) AROMATIC COMPOUNDS

(75) Inventors: Masayuki Takeuchi, Fukuoka (JP);
Masato Ikeda, Fukuoka (JP); Seiji Shinkai, Fukuoka (JP)

(73) Assignee: Kyushu University, National University Corporation, Fukuoka (JP)

( * ) Notice: Subject to any disclaimer, the term of this patent is extended or adjusted under 35 U.S.C. 154(b) by 175 days.

(21) Appl. No.: 10/538,484

(22) PCT Filed: Dec. 11, 2003

(86) PCT No.: PCT/JP03/15826

§ 371 (c)(1),
(2), (4) Date: Jun. 8, 2005

(87) PCT Pub. No.: WO2004/058684

PCT Pub. Date: Jul. 15, 2004

(65) Prior Publication Data

US 2006/0111587 A1    May 25, 2006

(30) Foreign Application Priority Data

Dec. 12, 2002 (JP) .............................. 2002-360369

(51) Int. Cl.
  *C07C 233/05*  (2006.01)
  *C07C 233/65*  (2006.01)
(52) U.S. Cl. ....................... 564/153; 430/55; 430/58.7; 564/17; 564/47; 564/48; 560/157

(58) Field of Classification Search ................ 564/153, 564/17, 47, 48; 430/55, 58.7; 560/157
See application file for complete search history.

(56) References Cited

FOREIGN PATENT DOCUMENTS

JP    58-209749    * 12/1983

OTHER PUBLICATIONS

Bacher et al, Macromolecules, 1999, 32, 4551-4557.*
Ramirez et al, The Journal of Organic Chemistry, vol. 33, No. 1., 1968, 20-24.*
Niels J. der Veen et al, J. Am. Chem. Soc., 2000, 122, 6112-6113.*

* cited by examiner

*Primary Examiner*—Shailendra Kumar
(74) *Attorney, Agent, or Firm*—Fay Sharpe LLP

(57) ABSTRACT

Disclosed is an aromatic compound expressed by the general formula (I), wherein A represents of a fused aromatic hydrocarbon moiety such as triphenylene, X represents a hydrogen-bonding site such as an atomic group containing an amide linkage, Y represents a chain functional group such as an alkyl group having 3 to 18, preferably 10 to 18 carbon atoms, and n represents an integer ranging from 2 to 10. The aromatic compound forms a molecular assembly in which the aromatic rings mutually overlap and exhibits an excellent charge carrier transfer property $$A\text{-}(X\text{---}Y)_n. \qquad (I)$$

3 Claims, 5 Drawing Sheets a)

b)

AROMATIC COMPOUNDS

This application is a 371 of PCT/JP03/15826, filed Dec. 11, 2003.

TECHNICAL FIELD

The present invention belongs to the technical field of functionalization of organic molecules and more particularly relates to novel aromatic compounds that are expected to have a wide variety of applications as, for example, charge transfer materials.

BACKGROUND

π-Electron excess (π-electron-rich) organic molecules are used as charge transfer materials or photoconductive materials in many fields such as organic electroluminescence devices, organic light-emitting diodes, photoelectric transducers, photoconductors for electrophotography, and liquid-crystal displays. In general, the organic molecules used for such purposes have an extended π-conjugation system or assume a structure in which the planar (disk-shaped) molecules with the π-electron system stack up or pile up, so that the transfer of charge carriers (positive holes) is efficiently effected. Examples of the latter type are disk-shaped fused aromatic hydrocarbons typified by triphenylene.

It is known that triphenylene, when introduced with long chain groups, exhibits liquid crystal properties and has high conductivity for an organic molecule. This is attributed to the stacking or columnar alignment of the disk-shaped molecules, which forms the so-called "discotic" liquid crystal structure. However, computational studies reveal that triphenylene molecules in mesogenic phase will not assume the configuration in which the four benzene rings completely overlap with one another (for example, see P. Etchegoin, Phys. Rev. E, 56, 538 (1997)).

Control of the molecular configuration of disk-shaped aromatic compounds, such as triphenylene, so as to realize a molecular assembly in which π-electron systems or aromatic rings completely overlap can be expected to contribute to the development of novel functional materials with an improved charge carrier transfer property or photoconductivity. However, no such technology is available so far.

The object of the present invention is to provide novel aromatic compounds suitable for use as charge carrier transfer materials and photoconductive materials.

DISCLOSURE OF THE INVENTION

Through extensive studies, the present inventors found, based on the design of molecules having a skeleton composed of a fused aromatic hydrocarbon such as triphenylene, a new type of organic compound with a π-electron system, whereby they achieved the present invention, wherein the molecules form a molecular assembly in which the aromatic rings may mutually overlap to the greatest extent (even completely if possible).

Therefore, according to the present invention, there is provided an aromatic compound expressed by the following general formula (I):

wherein A represents a fused aromatic hydrocarbon moiety or residue, X represents a hydrogen-bonding site, Y represents a chain functional group having 3 to 18 carbon atoms, and n represents an integer ranging from 2 to 10.

BEST MODE FOR CARRYING OUT THE INVENTION

Figure 1:
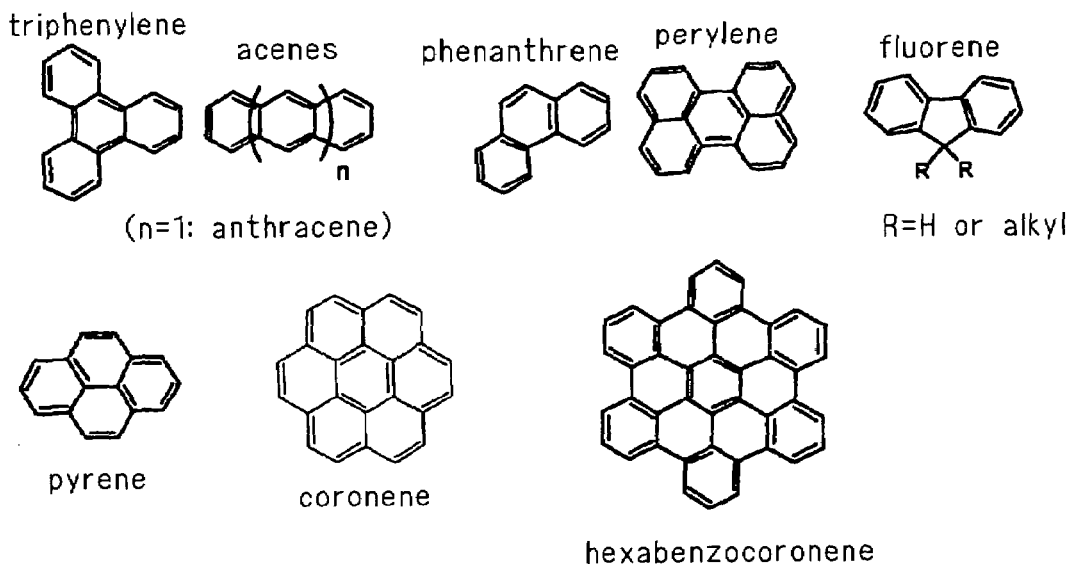
FIG. 1 shows examples of fused polyaromatic hydrocarbons for composing the aromatic compounds of the present invention.

As the fused aromatic hydrocarbon (A) for composing the skeleton of the compound of the present invention expressed by the aforementioned formula (I), a number of compounds with a substantially disk-shaped molecular structure known in the art may be applied. Preferred examples of the fused aromatic hydrocarbons include, but are not limited to, triphenylene, acenes (anthracene, naphthacene, pentacene, hexacene and heptacene), phenanthrene, perylene, fluorene, pyrene, coronene and hexabenzocoronene. The chemical structures of these fused aromatic hydrocarbons are shown in FIG. 1 (In the structural formulae shown in the present specification and drawings, hydrogen and carbon atoms may be omitted according to the commonly used chemical notation).

As shown by the formula (I), the aromatic compounds of the present invention have a plurality of (n=2-10) chain groups comprising hydrogen-bonding sites (X) and chain functional groups (Y) bound to the above-mentioned fused aromatic hydrocarbon moiety, thus providing a distinctive feature over the conventionally known disk-shaped molecules or compounds with a π-electron system in which only chain functional groups are introduced to the triphenylene moiety.

Figure 2:
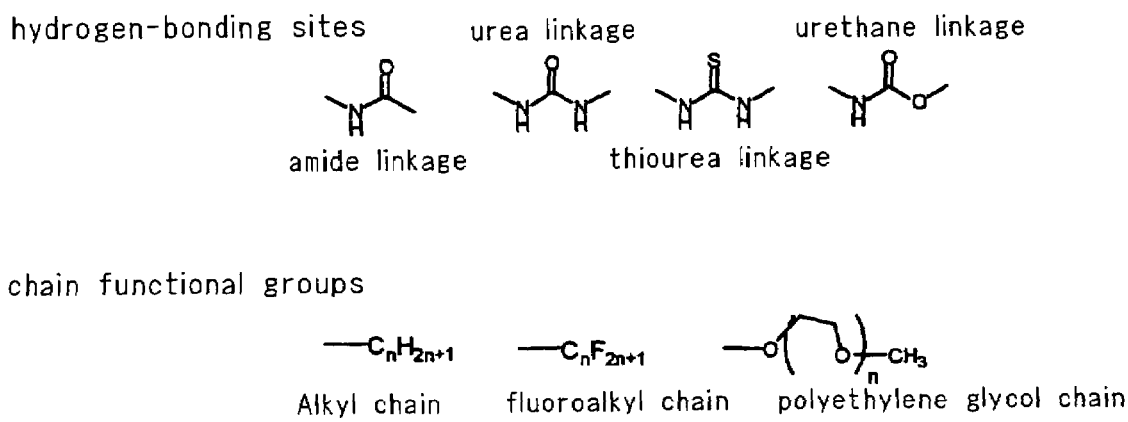
FIG. 2 shows examples of hydrogen-bonding sites and chain functional groups for composing the aromatic compound of the present invention.

Preferred hydrogen-bonding sites include, but are not limited to, atomic groups containing an amide linkage, a urea linkage, a thiourea linkage and an urethane linkage. The chain functional group is typically an alkyl group, but fluoroalkyl and polyethyleneglycol groups are also applicable. In general, the chain functional group has a length of 3 to 18 carbon atoms and, as will be explained later, the chain length affects the configurational characteristic of the disk-shaped molecules. The structural formulae of preferred examples of the hydrogen-bonding sites and the chain functional groups are shown in FIG. 2.

The above-mentioned aromatic compounds of the present invention function to gelate some organic solvents, generally non-polar hydrocarbon solvents, and the structure of the assembly (gel) is retained as the solid state or as the cast film evaporated from said organic solvents.

Spectroscopic, X-ray diffraction and other studies show that the molecular assembly formed from an aromatic compound of the formula (I) of the present invention assumes a molecular configuration in which the aromatic rings or the π-electron systems mutually overlap. Particularly, a molecular assembly formed from the aromatic compound with long alkyl chain groups (10 to 18 carbon atoms) may assume a configuration in which all the aromatic rings completely overlap with one another.

This is presumably attributed to the fact that the overlapping among the respective molecules is favorably enhanced by the hydrogen-bonding interactions and, particularly in the presence of long chain functional groups, the van der Waals interactions, as well as the associative interactions between the aromatic rings, so as to form a stable configuration in which all the aromatic rings overlap completely with one another (see Example 4, to be described later).

Figure 3:
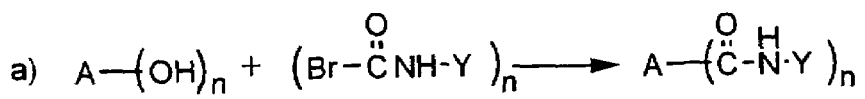
FIG. 3 shows examples of the reaction scheme for synthesizing the aromatic compounds of the present invention.
Figure 3:
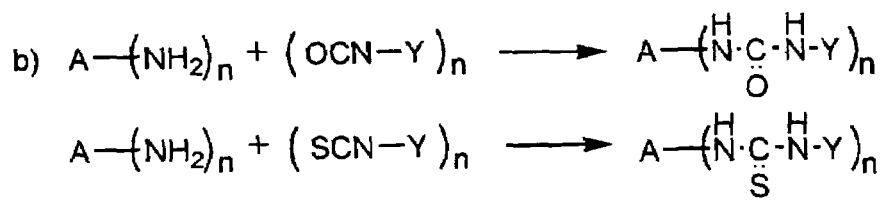
Figure 4:
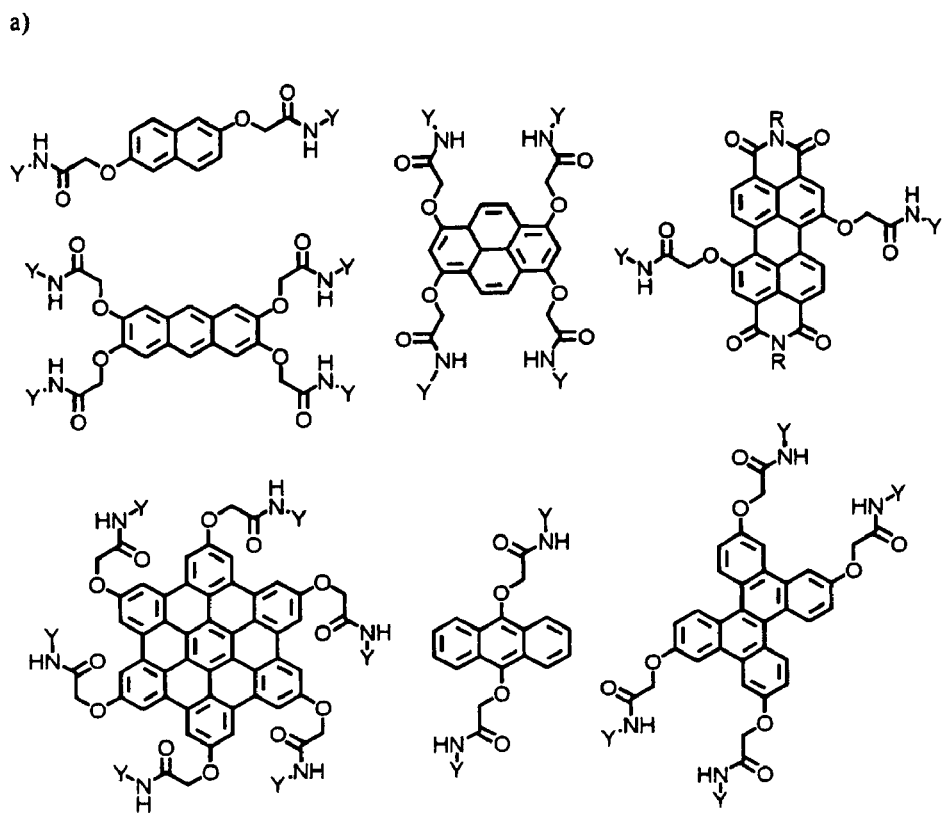
FIG. 4 shows some examples of structural formulae of the aromatic compounds of the present invention.
Figure 4:
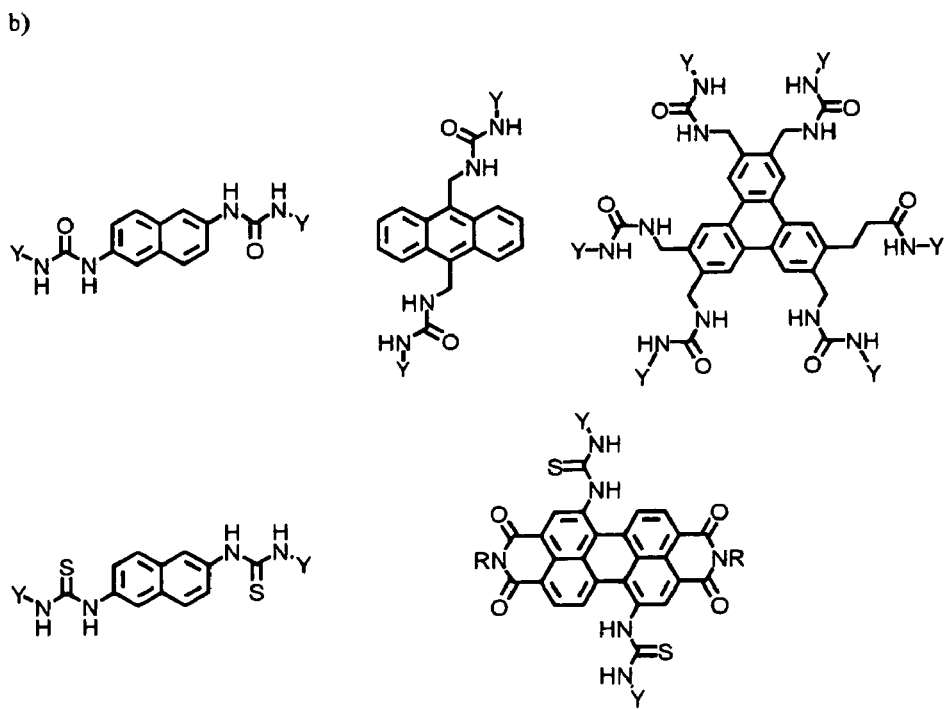
Figure 5:
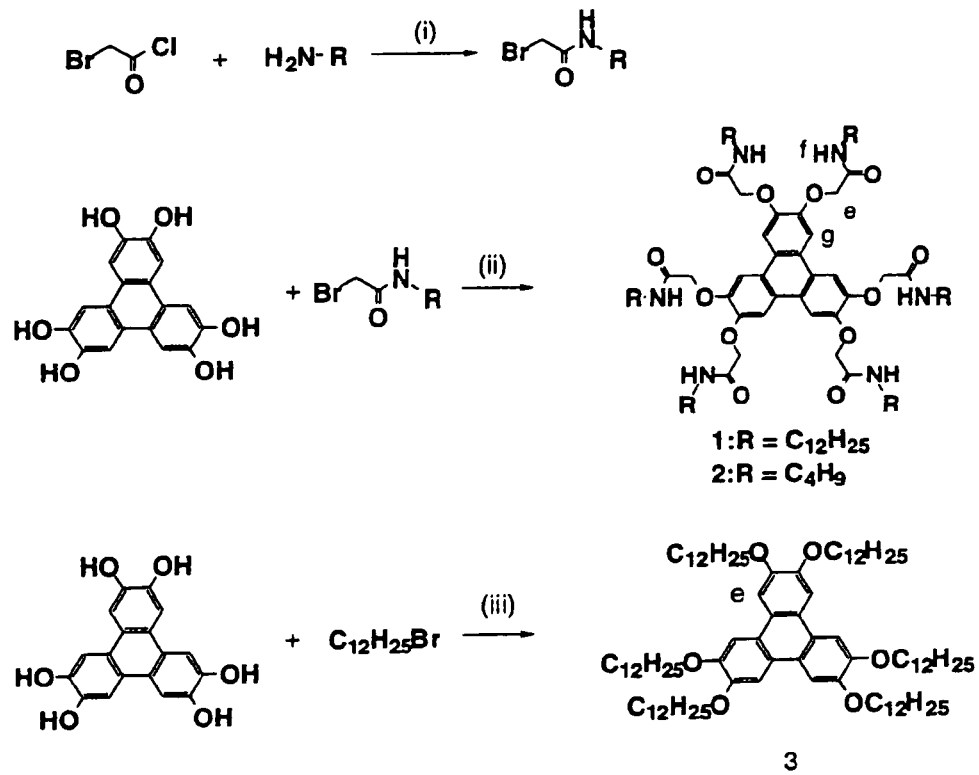
FIG. 5 illustrates the reaction scheme for synthesizing an example of triphenylene-based aromatic compounds of the present invention.

The aromatic compounds of the present invention can be synthesized by utilizing reactions known in the art. For example, the aromatic compound of the present invention with an amide linkage as the hydrogen-bonding site can be synthesized by the Williamson reaction of a fused aromatic hydrocarbon substituted with one or more hydroxyl groups with an amide compound having a halogen atom such as bromine at the terminal thereof, as typically shown in FIG. 3a. The aromatic compound of the present invention with a urea or thiourea linkage as the hydrogen-bonding sites can be synthesized by the reaction of a fused aromatic hydrocarbon substituted with one or more amino groups with an isocyanate or thioisocyanate compound, as typically shown in FIG. 3b. The examples of the structural formulae of the aromatic compounds of the present invention synthesized by the reactions as shown by FIG. 3a or FIG. 3b are shown in FIG. 4. FIG. 5 illustrates the reaction scheme to synthesize examples of the aromatic compounds of the present invention in a more specific manner, wherein the fused aromatic hydrocarbon is triphenylene.

In a preferred example of the aromatic compounds of the present invention, the fused polyaromatic hydrocarbon is triphenylene and thus, for a particularly preferred compound the formula (I) is expressed by the following formula (II):

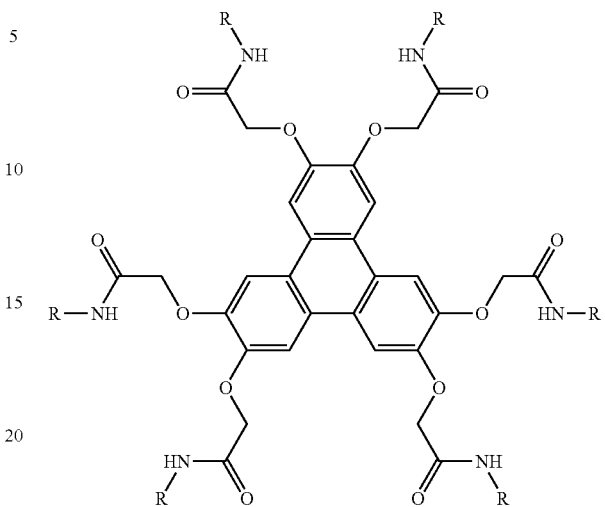

(II)

wherein R represents an alkyl group having 3 to 18 carbon atoms. When R is an alkyl group having 10 to 18 carbon atoms, it is found that the compound assumes a configuration in which all the four aromatic rings mutually overlap.

An aromatic compound of the present invention can be obtained as a solid powder by forming an organogel from the compound with an appropriate organic solvent followed by the evaporation of the solvent to dryness to produce a molecular assembly of the aromatic compound as the solid powder.

Hereinafter, examples of the present invention will be described to illustrate the features of the present invention more specifically. However, the scope of the invention is not limited to these examples.

EXAMPLE 1

Synthesis of the Aromatic Compounds

According to the reaction scheme outlined in FIG. 5 ((i) and (ii)), there were synthesized compounds 1 and 2 corresponding to the above mentioned formula (II), in which R=$C_{12}H_{25}$ and $C_4H_9$, respectively, as aromatic compounds of the present invention. As a reference, the compound 3 known in the prior art in which only long chain groups ($OC_{12}H_{25}$) are introduced to triphenylene was also synthesized.

Synthesis of 1-bromoacetyldodecyl Amide:

Dodecylamine (5 g, 26.97 mmol), TEA (3.7 ml, 1.1 eq.) and dry dichloromethane (100 ml) were added to a 200 ml of double-necked flask fitted with a dropping funnel in a nitrogen stream. Bromoacetyl chloride (2.23 ml, 1 eq.) in dry dichloromethane (50 ml) was added dropwise to the mixture under cooling in an ice bath. After the addition, the mixture was stirred overnight at room temperature, followed by the removal of the insoluble material. The mixture was washed with distilled water (200 ml×2) and then subjected to flush column chromatography (silica gel; chloroform:methanol=10:1) to remove the components at the original point. The compound thus obtained was used in the next step without further purification.

Synthesis of Compound 1:

In a 100 ml double-necked flask, 2,3,6,7,10,11-hexahydroxytriphenylene (300 mg, 0.92 mmol) was dissolved in dry DMF (25 ml) in a nitrogen stream. To the solution were added finely ground potassium carbonate (1.28 g, 6.0 eq.) and 1-bromoacetyldodecyl amide (1.86 g, 6.6 eq.) and the resultant mixture was stirred overnight at 60° C. There was added 200 ml of distilled water and the precipitate was collected by filtration and washed with methanol. The crude product was dissolved in chloroform and purified by column chromatography (silica gel; chloroform:methanol=10:1) to give compound 1 as white solid (800 mg/52%). The product was identified by MALDI-TOF-MS, elemental analysis and $^1$H-NMR (see Table 1).

MALDI-TOF-MS (CHCA): m/z 1700.05 (Calcd for $[M+Na]^+$11715.605); Anal. Calcd for $C_{102}H_{174}N_6O_{12}$: C, 73.07; H, 10.46; N, 5.01%. Found: C, 72.17; H, 10.21: N, 4.80%.

TABLE 1

| | $^1$H-NMR(RT, CDCl$_3$, 600MHz, TMS standard) | | | |
|---|---|---|---|---|
| δ | split (J/Hz) | integral ratio | theoretical ratio | assignment |
| 0.87 | t | 17.8 | 18H | a(C$\underline{H}_3$) |
| 1.11-1.29 | m | 120.5 | 108H | b(CH$_3$C$\underline{H}_2$) |
| 1.54-1.58 | m | — | 12H | c(NHCH$_2$C$\underline{H}_2$) |
| 3.38 | q | 18.0 | 12H | d(NHC$\underline{H}_2$) |
| 4.75 | s | 14.8 | 12H | e |
| 6.84 | s | 5.4 | 6H | f |
| 7.79 | s | 6.0 | 6H | g |

Synthesis of Compound 2:

Synthesis was carried out in a manner similar to the synthesis of compound 1 using butylamine instead of dodecylamine and the identification of the product was conducted.

Synthesis of Compound 3:

In a 100 ml double-necked flask, 2,3,6,7,10,11-hexahydroxytriphenylene (50 mg, 0.15 mmol) was dissolved in dry DMF (5 ml) in a nitrogen stream. To the solution were added finely ground potassium carbonate (0.13 g, 6.0 eq.) and dodecyl bromide (246.7 mg, 6.6 eq.) and the resultant mixture was stirred overnight at 60° C. There was added 200 ml of distilled water and the precipitate was collected by filtration and washed with methanol. The crude product was dissolved in chloroform and purified by column chromatography (silica gel; hexane: chloroform=2:1) to give compound 3 as white solid (70 mg/35%). The product was identified by MALDI-TOF-MS, elemental analysis and $^1$H-NMR (see Table 2).

MALDI-TOF-MS (CHCA): m/z 1334.82 (Calcd for $[M+H]^+$1334.50); Anal. Calcd for $C_{90}H_{156}O_6 \cdot 0.75CHCl_3$: C, 76.56; H, 11.10%. Found: C, 76.45; H, 11.52%.

TABLE 2

| | $^1$H-NMR(RT, CDCl$_3$, 600MHz, TMS standard) | | | |
|---|---|---|---|---|
| δ | split (J/Hz) | integral ratio | theoretical ratio | assignment |
| 0.86 | t | 20.0 | 18H | a(C$\underline{H}_3$) |
| 1.20-1.55 | m | 196.3 | 108H | b(C$\underline{H}_2$) |
| 1.97 | m | 18.2 | 12H | c(OCH$_2$C$\underline{H}_2$) |

TABLE 2-continued

| | $^1$H-NMR(RT, CDCl$_3$, 600MHz, TMS standard) | | | |
|---|---|---|---|---|
| δ | split (J/Hz) | integral ratio | theoretical ratio | assignment |
| 4.23 | q | 13.9 | 12H | d(OC$\underline{H}_2$) |
| 7.83 | s | 6.0 | 12H | e |

Synthesis of Compound 4:

As another example of the aromatic compound of the present invention, compound 4 of the following formula (III) was synthesized.

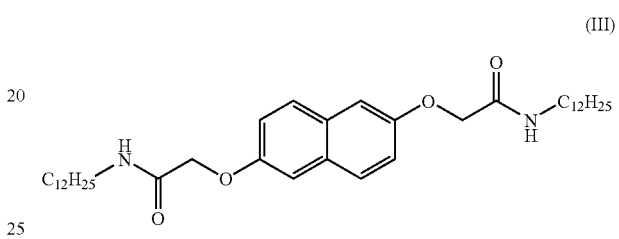

(III)

To a solution of 2,7-dihydroxynaphthalene (160 mg, 1.0 mmol) in dry DMF, were added finely ground potassium carbonate (400 mg, 2.0 mmol) and 1-bromoacetyldodecyl amide (620 mg, 2.2 eq.) and the resultant mixture was stirred overnight at 60° C. There was added 200 ml of distilled water and the precipitate was collected by filtration and washed with methanol. The crude product was dissolved in a solvent in which it is soluble (chloroform) and purified by column chromatography (silica gel) and recrystalization to give compound 4 as white powder (425 mg/70%). The product was identified by MALDI-TOF-MS, elemental analysis and $^1$H-NMR.

MALDI-TOF-MS (CHCA): m/z 611.52 (Calcd for $[M+H]^+$611.47); $^1$H-NMR (TMS standard/ppm, CDCl$_3$, RT) δ 0.87 (t, 6H), 1.29-1.55 (m, 40H), 3.20 (q, 4H), 4.93 (s, 4H), 6.96 (2H), 7.04 (2H), 7.58 (2H).

Synthesis of Compound 5:

As still another example of the aromatic compound of the present invention, compound 5 of the following formula (IV) was synthesized.

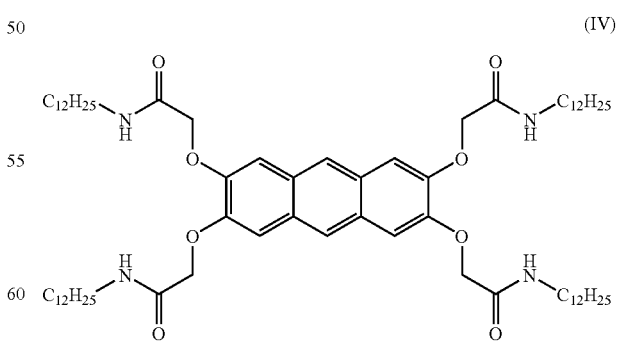

(IV)

To a solution of 2,3,6,7-tetrahydroxyanthracene (242 mg, 1.0 mmol) in dry DMF, were added finely ground potassium carbonate (800 mg, 4.0 mmol) and 1-bromoacetyldodecyl amide (1.3 g, 4.4 eq.) and the resultant mixture was stirred overnight at 60° C. 200 ml of distilled water was added and the precipitate was collected by filtration and washed with methanol. The crude product was dissolved in a solvent in which it is soluble (chloroform) and purified by column chromatography (silica gel) and recrystalization to give compound 4 as white powder (425 mg/70%). The product was identified by MALDI-TOF-MS, elemental analysis and $^1$H-NMR.

MALDI-TOF-MS (CHCA): m/z 1144.12 (Calcd for [M+H]$^+$1143.89); $^1$H-NMR (TMS standard/ppm, CDCl$_3$, RT) δ 0.92 (t, 12H), 1.26-1.57 (m, 80H), 3.24 (q, 8H), 4.88 (s, 8H), 7.20 (4H), 8.08 (2H).

EXAMPLE 2

Gel Formation and Absorption Spectra

This example demonstrates that the aromatic compounds of the present invention form the molecular assemblies (organogels) through π-π interaction in appropriate organic solvents.

Gelation Test

To a septum-capped test tube (i.d. 5 mm) were added compounds 1 or 2 and a solvent (100 µl) so that the concentration of the resultant solution was 10 mM and the solution was sonicated and heated with a heat gun until the solid was dissolved. After standing for 30 minutes at room temperature, the sample was turned upside down and judged visually. When the sample did not flow, it was judged to be a gel. The samples with no observed gel formation were subjected to standing at a lower temperature for further judgment.

The gelation abilities of compounds 1 and 2 are shown in Table 3. As seen from Table 3, compound 1 exhibited a gelation ability particularly for non-polar hydrocarbon solvents. Compound 3 exhibits a high solubility and no gelation was observed.

TABLE 3

| Solvent | 1 | 2 |
|---|---|---|
| Ethanol | I | I |
| Hexanol | P | I |
| Ethyl acetate | I | I |
| Hexane | G | I |
| Octane | G | I |
| Cyclohexane | G | pG |
| p-Xylene | G | P |
| Benzene | S | P |
| Toluene | S | P |
| Chloroform | S | S |
| Carbon tetrachloride | S | S |
| Tetrahydrofuran | S | P |
| Diphenyl ether | S | S |

I = insoluble
S = soluble
P = precipitate
G = gel
pG = partial gel

Measurement of Absorption Spectra

Absorption spectra were measured with respect to the cyclohexane gels of compounds 1 and 2, and the chloroform solutions in which these compounds dissolved without forming gels. Samples were prepared by dropping the gel at a given concentration on a quartz plate followed by sandwiching with another quartz plate. The chloroform solutions (each 2.5×10$^{-5}$ mol) were confirmed to assume a monodispersed system through the Lambert-Beer plot.

Figure 6:
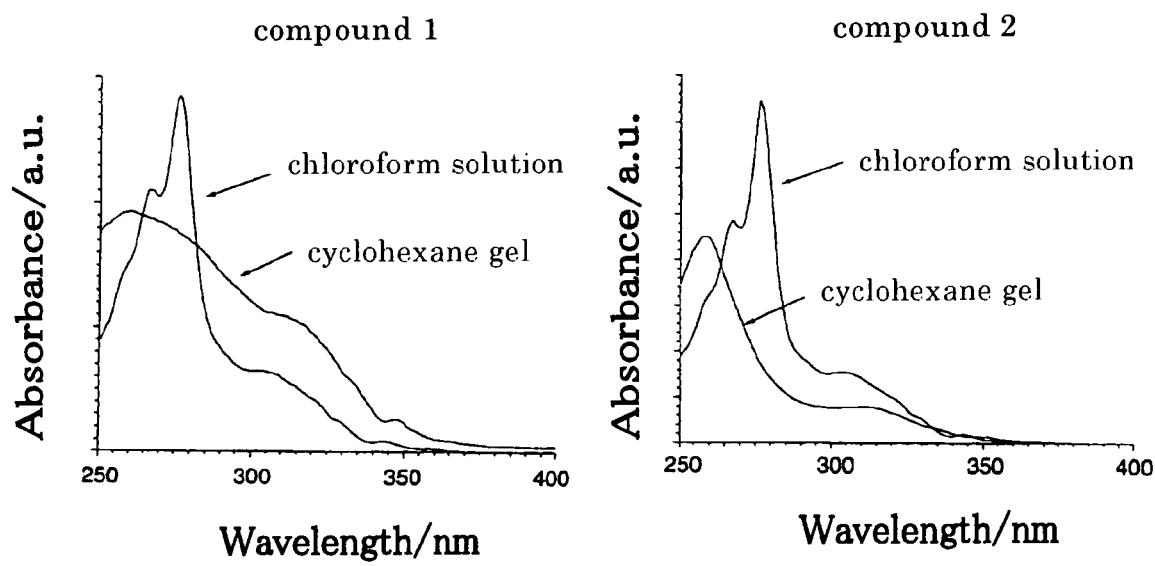
FIG. 6 shows examples of absorption spectra of an organic gel and an organic solvent solution prepared from an aromatic compound of the present invention.

The absorption spectra thus obtained are shown in FIG. 6. It is suggested that triphenylene moieties of each of compounds 1 and 2 stand close so that they interact with each other in the ground state. The spectral patterns are only slightly different and similar as a whole between the compounds, suggesting that these compounds assume an associated state similar to each other. Thus, it is suggested that the triphenylene moieties of these compounds assume a stacked configuration in which the moieties mutually overlap. The peaks around 340 nm assignable to the transition to singlet excited state (S$_0$→S$_1$) shifted to a longer wavelength.

Absorption spectra with varying temperature showed that upon elevating the temperature, the peak broadening disappeared at the temperature of the sol-gel transition, suggesting the occurrence of π-π interaction in the gel.

EXAMPLE 3

Determination of the Structure by XRD and Other Methods

This example show the results of the X-ray powder diffraction (XRD) and IR (infrared spectroscopy) measurements of the gel of compound 1 prepared according to the Example 2 in order to determine its structure.

XRD Measurement

XRD measurement was carried out on the solid sample prepared by removing the solvent from the cyclohexane gel of compound 1 at room temperature with an evaporator. The powder sample was loaded in a capillary of 0.7 mm diameter. The powder sample of compound 2 was prepared by removing the solvent from the partially gelated cyclohexane solution at room temperature with an evaporator and the powder sample thus obtained was loaded in a capillary of 0.7 mm diameter.

Figure 7:
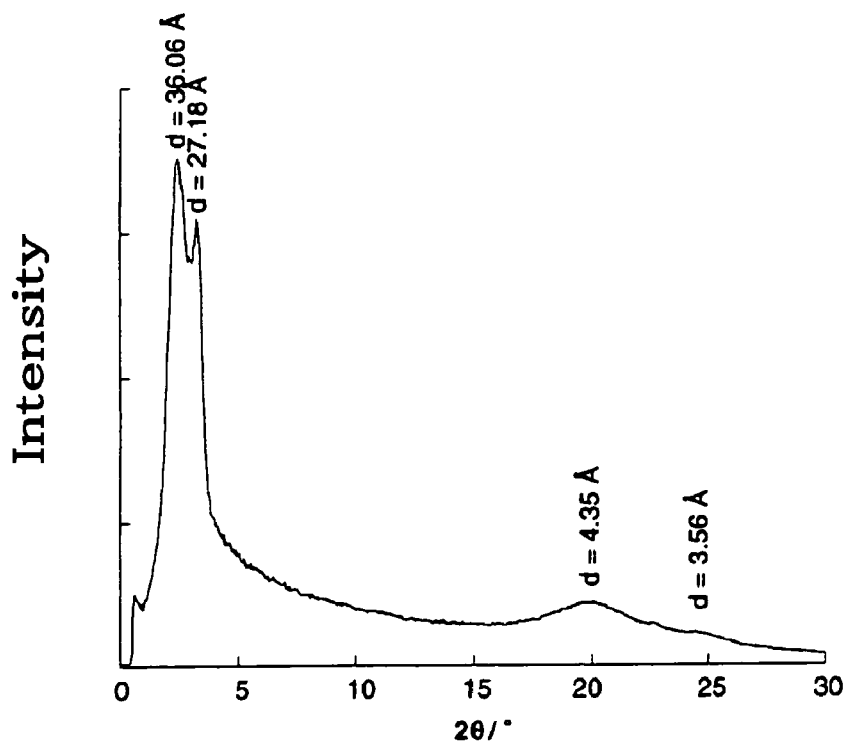
FIG. 7 shows the X-ray powder diffraction spectrum of an example of the aromatic compounds of the present invention.

The XRD spectrum of the powder prepared from the cyclohexane gel of compound 1 is shown in FIG. 7. There were observed two peaks of d=4.35 Å and 3.56 Å in the wide angle range of 2θ=20-30°. The two peaks are assigned to the diffractions from the disordered dodecyl long chain and the distance between triphenylene moieties (disks), respectively. The values of the peaks were comparable to those observed in triphnylene-based liquid crystals. Two peaks are also observed in the low angle range which reflects two dimensional ordered structure. From these results, it is understood that compound 1 of the present invention forms a molecular assembly in which the respective molecules stack up in a columnar structure. However, the absence of the peak around 2θ=5°, characteristic of the two-dimensional ordered structure of a discotic liquid crystal, suggests that two-dimensionally ordered packing (such as hexagonal) does not exist in the gel.

The result of the XRD measurement of the powder prepared from the cyclohexane gel of compound 2 was similar to that of the sample prepared from compound 1. There was observed a peak corresponding to the distance between triphenylene moieties (d=3.58 Å), which is approximately equal to the peak of FIG. 7 observed for compound 1. However, no peak assignable to the disordered alkyl chains was observed because compound 2 has short alkyl chains.

IR Measurement

Samples were prepared by adding cyclohexane or chloroform to compound 1 or 2 to give a concentration of 5 mM. The samples were cast on a substrate (quartz), dried in the air, and subjected to IR measurement.

The peak assignable to the amide I band (C=O stretching) was observed at 1655 cm$^{-1}$ because of the hydrogen-bonding interactions. The amide II band (N—H bending) was observed at around 1622 cm$^{-1}$ as a shoulder. There were also observed the NH stretching bands at 3275 cm$^{-1}$ and around 3095 cm$^{-1}$. These results suggest that there are hydrogen-bonding interactions in the assemblies of both compound 1 and 2 independently from the solvent used for casting.

EXAMPLE 4

Determination of the Structure by Fluorescence Spectroscopic Measurement

The present examples show the results of a further study on the structure of the gels prepared from the aromatic compounds of the present invention and particularly demonstrate that the gel prepared from compound 1 assumes a configuration in which all the four aromatic rings mutually overlap.

Fluorescence Spectroscopic Measurements of Compounds 1,2, and 3 in the Solutions and the Gels Gels were prepared from compounds 1 and 2 with cyclohexane (hereinafter referred to as cyclohexane gel(s)). The concentration of compound 1 or 2 in cyclohexane was adjusted to 5 mM. Chloroform solutions of compounds 1, 2 and 3 (5×10$^{-5}$ M) were also prepared. The fluorescence spectroscopic measurement was carried out for each gel. The excitation wavelength $\lambda_{ex}$ for the measurements was 340 nm.

Figure 8:
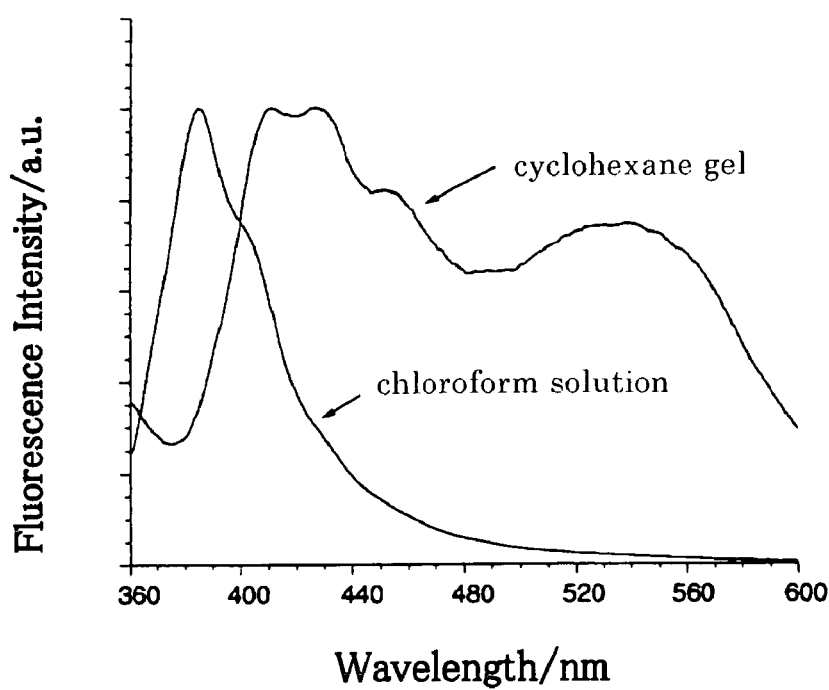
FIG. 8 shows the fluorescence spectra of an example of the aromatic compounds of the present invention.

The results for compound 1 are shown in FIG. 8. As seen from the figure, the fluorescence spectrum of compound 1 in chloroform solution was similar to the spectrum of the conventionally known triphenylene derivative with long polyether groups. However, in the cyclohexane gel, the fluorescence maxima shifted to a longer wavelength, and further a new broad emission band around 525 nm was observed. No significant change was observed in the shape of the spectra upon varying the excitation wavelength around 340 nm. In the excitation spectrum of the cyclohexane gel an absorption was observed (at the wavelength around 340 nm) assignable to the transition to singlet excitation state ($S_0 \rightarrow S_1$). Considering these results, together with the wavelength of 520 nm as previously reported for the excimer emission of triphenylene film cooled to –170° C. (J. B. Birks, Rep. Prog. Phys., 38, 903 (1975)), the fluorescence at 525 nm is assignable to the excimer emission. One can also assume that the longer wavelength shift of the emission is attributable to the influence of the assembly on the energy of ground state.

Similar measurements were also carried out for compound 2. For the cyclohexane gel of compound 2, there was observed no broad fluorescence band at around 525 nm as observed for compound 1, and only a red-shifted fluorescence was observed. No significant change was observed in the shape of the spectrum upon varying the excitation wavelength around 340 nm (see FIG. 9).

Figure 10:
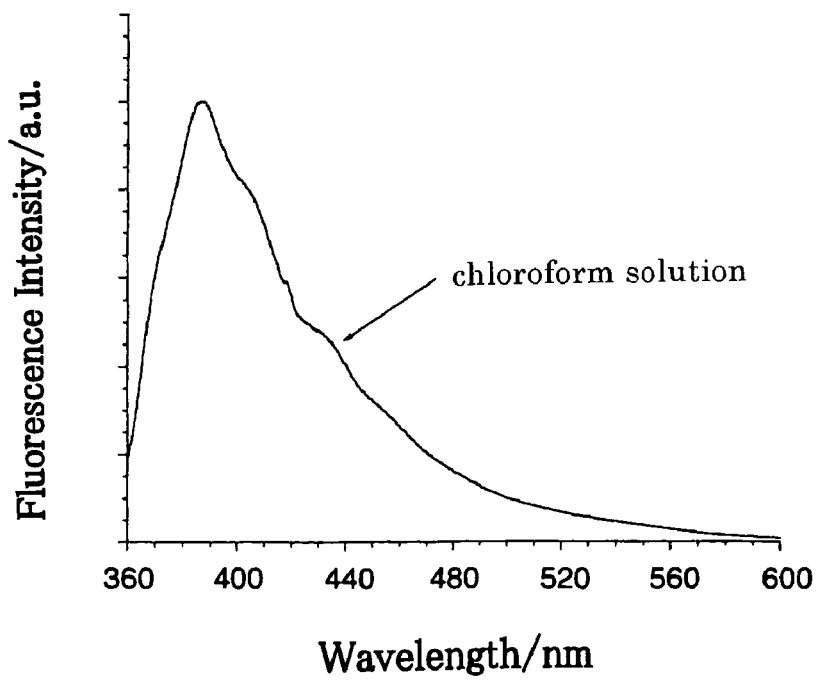
FIG. 10 shows the fluorescence spectra of a compound taken as a reference with respect to the compounds of the present invention.

Compound 3 was soluble in both cyclohexane and chloroform and exhibited the fluorescence spectra shown in FIG. 10. No fluorescence at around 525 nm was observed and no red-shifted fluorescence was observed either.

Solid-State Fluorescence Measurement

Figure 9:
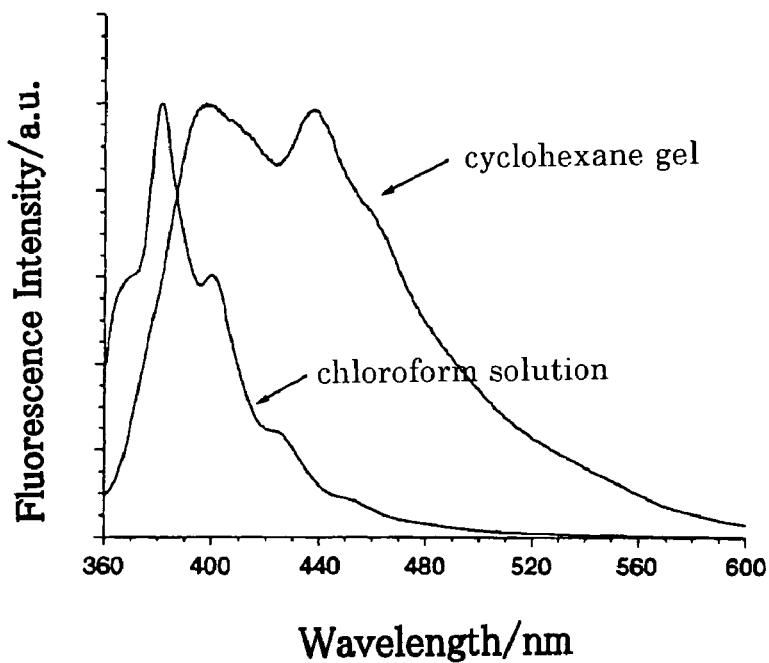
FIG. 9 shows the fluorescence spectra of another example of the aromatic compounds of the present invention.

As both compounds 1 and 2 were soluble in hot cyclohexane, solid samples were prepared by dissolving the compounds in cyclohexane followed by removing the solvent with a rotary evaporator at room temperature. Each of the solid samples thus prepared was then subjected to fluorescence spectroscopic measurement. As shown in FIG. 8 and FIG. 9, the difference in the spectra reflecting the difference in the gel was also observed in the solid state. Therefore, it was confirmed that the assembly structure of the gel is maintained even in the solid state.

As pointed out above, only the assembly structure of compound 1 due to the formation of the gel exhibited the strong excimer emission. An 'excimer' is an excited dimer composed of a species at excited state and the same species at ground state. When an excimer forms, an emission from the excimer at a longer wavelength is ordinarily observed together with the emission from the excited monomer. The above-mentioned results support the conclusion that the gel prepared from compound 1 falls under to such system.

In the formation of an excimer, the overlapping of $P_z$ orbitals play an important role. For example, it is known that in a cyclophane composed of phenanthrenes the excimer emission is observed only when aromatic rings entirely overlap. It is understood that in the molecular assembly (gel) of compound 1 of the present invention formed with a solvent such as cyclohexane, the molecules in the ground state assume a configuration favorable to the excimer formation in which aromatic rings entirely overlap and the excimer will form rapidly upon excitation.

It is speculated that one of the contributing factors in such configurational control occurring in the compounds of the present invention such as compound 1 is the introduction of hydrogen-bonding groups such as amide groups (amide linkages). More specifically, the arrangement (overlapping) of the molecules will be enhanced through the associative interactions between the aromatic rings as well as the hydrogen-bonding interactions. In addition, the presence of the chain functional groups such as alkyl groups will also have an effect. The compounds with short alkyl groups such as compound 2 form an assembly in which the aromatic rings will adopt a staggered or somewhat off-centered overlap as in the conventional triphenylene-based liquid crystal, while the compounds with long alkyl groups such as compound 1 form an assembly in which the aromatic rings completely overlap with one another in a stabilized, eclipsed configuration.

EXAMPLE 5

Charge Carrier Mobility Measurement

This example demonstrates the excellent charge carrier transfer property of the aromatic compounds of the present invention.

Preparation of the Compound:

The gel was prepared in a manner similar to that in Example 2, by dissolving compound 1 in cyclohexane under heating. The concentration of the compound in cyclohexane was adjusted to 5 mM. The cyclohexane gel thus obtained was removed of solvent using a rotary evaporator and the resultant powder was subjected to the measurement.

Determination of the Conditions of Charge Carrier Mobility Measurement:

Before measuring the charge carrier mobility, the temperature range over which the hydrogen-bonding interaction, one of the dominant factors controlling the configuration of compound 1, existed was investigated by means of a variable-temperature infrared spectrometer. The stretching vibration band of the amide group was observed at 3272-

3292 cm$^{-1}$ over the temperature range of room temperature to 250° C., indicating strong intermolecular hydrogen-bonding interaction. Above 260° C. the peaks shifted to 3389 and 3343 cm$^{-1}$, which implies that the hydrogen-bonding interaction was weakened and the stacking was only through the π-π stacking interaction among the aromatic moieties. Differential scanning calorimetry (DSC) measurement showed that compound 1 had a stable ordered structure in the range of 100 to 260° C. From these results, it was decided to carry out the measurement at a temperature of 160° C. A polarization microscopic observation showed that the texture remained unchanged over the temperature range of 100 to 260° C., supporting the presence of the stably controlled configuration.

Methods and Results:

The measurement was carried out by the known method described in the literature (N. Boden, R. J. Bushby, J. Clements, B. Movagher, K. J. Donovan and T. Kreouzis, Phys. Rev. B, 1995, 52, 13274). The sample of aromatic compound 1 prepared as explained above was loaded between two electrodes spaced at a certain distance (16 μm) and the photoconductivity was measured with a time-of-flight apparatus. The result can be obtained as transient time (tT) from the inflection point of a log-log plot of time vs. photocurrent and the charge carrier (hole) mobility μ can be calculated from the following equation:

$$\mu = d/E \cdot tT$$

wherein d represents the thickness of the sample and E represents the applied voltage.

For compound 1, there was obtained a value of the charge carrier mobility μ=2.1×10$^{-2}$/cm$^{-2}$ V$^{-1}$ s$^{-1}$. In contrast, the charge carrier mobility of alkoxytriphenylene of the formula (V), which is similar in structure to compound 1 of the present invention but has no hydrogen-bonding site is reported to be 1×10$^{-3}$-10$^{-4}$/cm$^{-2}$ V$^{-1}$ s$^{-1}$ (the above-mentioned paper by N. Boden et al.), which is known as the highest value for the alkoxytriphenylene derivatives. Thus, compound 1 exhibits a charge carrier mobility much higher than that of such alkoxytriphenylene derivatives. This fact indicates that the aromatic compounds of the present invention with hydrogen-bonding sites are useful as a charge transfer material.

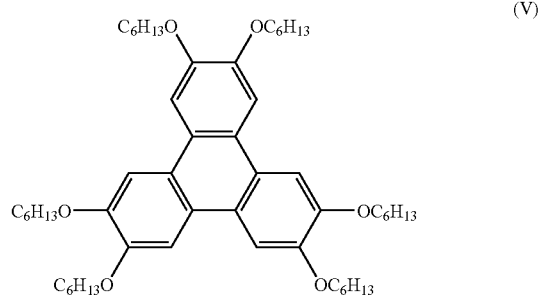

(V)

INDUSTRIAL APPLICABILITY

As understood from the foregoing description, the present invention provides novel aromatic compounds that are useful as functional materials such as charge transfer materials.

The invention claimed is:

1. An aromatic compound expressed by the following general formula (I):

A—(X—Y)$_n$  (I)

wherein A represents a fused polyaromatic hydrocarbon moiety selected from among triphenylene, acenes, phenanthrene, perylene, fluorene, pyrene, coronene and hexabenzocoronene, X represents a hydrogen-bonding site selected from among atomic groups containing an amide linkage, an urea linkage, a thiourea linkage or an urethane linkage, Y represents a chain functional group having 3 to 18 carbon atoms, and is selected from among an alkyl group, a fluoroalkyl group and a polyethylene glycol group, and n represents an integer ranging from 2 to 10.

2. An aromatic compound expressed by the following general formula (I):

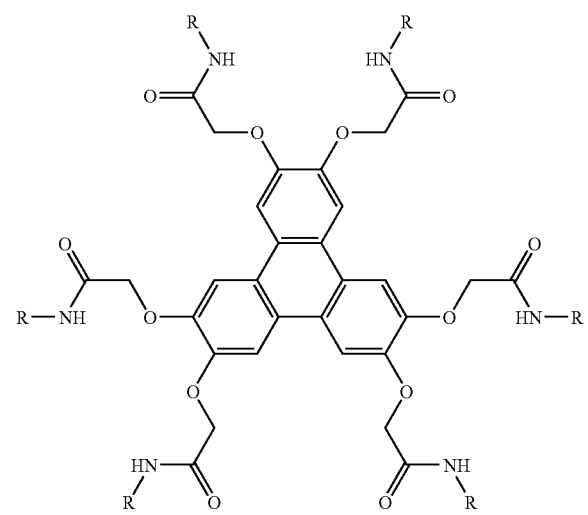

wherein R represents an alkyl group having 3 to 18 carbon atoms.

3. The aromatic compound according to claim 2, wherein said R is an alkyl group having 10 to 18 carbon atoms.

* * * * *